United States Patent
Chakrabarti et al.

(10) Patent No.: US 12,098,124 B2
(45) Date of Patent: Sep. 24, 2024

(54) ACID CATALYZED SYNTHESIS OF METHYL ACRYLATE FROM ACRYLIC ACID AND METHANOL

(71) Applicant: Rohm and Haas Company, Collegeville, PA (US)

(72) Inventors: Reetam Chakrabarti, Phoenixville, PA (US); Minh N. Ngo, Philadelphia, PA (US); James Elder, Friendswood, TX (US)

(73) Assignee: Rohm and Haas Company, Collegeville, PA (US)

( * ) Notice: Subject to any disclaimer, the term of this patent is extended or adjusted under 35 U.S.C. 154(b) by 523 days.

(21) Appl. No.: 17/600,764

(22) PCT Filed: Apr. 2, 2020

(86) PCT No.: PCT/US2020/026283
§ 371 (c)(1),
(2) Date: Oct. 1, 2021

(87) PCT Pub. No.: WO2020/214423
PCT Pub. Date: Oct. 22, 2020

(65) Prior Publication Data
US 2022/0162149 A1    May 26, 2022

Related U.S. Application Data

(60) Provisional application No. 62/834,462, filed on Apr. 16, 2019.

(51) Int. Cl.
C07C 67/08     (2006.01)
B01D 3/14      (2006.01)
(Continued)

(52) U.S. Cl.
CPC .............. C07C 67/08 (2013.01); B01D 3/146 (2013.01); B01J 27/02 (2013.01); B01J 31/0225 (2013.01);
(Continued)

(58) Field of Classification Search
CPC ......... C07C 67/08; C07C 67/54; C07C 67/58; C07C 69/54; B01D 3/146
See application file for complete search history.

(56) References Cited

U.S. PATENT DOCUMENTS 4,280,010 A    7/1981  Erpenbach et al.
5,945,560 A *  8/1999  Iffland ................. C07C 67/54
                                                     560/205

(Continued)

Primary Examiner — Yate' K Cutliff
(74) Attorney, Agent, or Firm — Brian L. Mutschler

(57) ABSTRACT

A method for preparing methyl acrylate comprises:
a) heating in a reaction zone a mixture comprising acrylic acid, methanol, and an acid catalyst to react and form a reaction product comprising methyl acrylate which is vaporized with other light components and then fed to a distillation zone, wherein a feed stream entering the reaction zone comprises methanol to acrylic acid in a molar ratio of greater than 1 and less than 2, and a residence time in the reaction zone ranges from 0.25 to 2 hours;
b) condensing and phase-separating a distillate from the distillation zone to form an organic phase comprising methyl acrylate and an aqueous phase;
c) returning a portion of the organic phase to the distillation zone as organic reflux; and
d) feeding the remainder of the organic phase and the aqueous phase of the distillation zone to an extraction column to form a methanol rich aqueous effluent and an organic effluent comprising methyl acrylate.

10 Claims, 1 Drawing Sheet

(51) Int. Cl.
 - *B01J 27/02* (2006.01)
 - *B01J 31/02* (2006.01)
 - *C07C 67/54* (2006.01)
 - *C07C 67/58* (2006.01)
 - *C07C 69/54* (2006.01)

(52) U.S. Cl.
 CPC .............. *C07C 67/54* (2013.01); *C07C 67/58* (2013.01); *C07C 69/54* (2013.01)

(56) References Cited

U.S. PATENT DOCUMENTS

| | | |
|---|---|---|
| 9,796,651 B2 | 10/2017 | Fauconet et al. |
| 2004/0236143 A1* | 11/2004 | Martan .................. C07C 67/08 560/205 |

\* cited by examiner

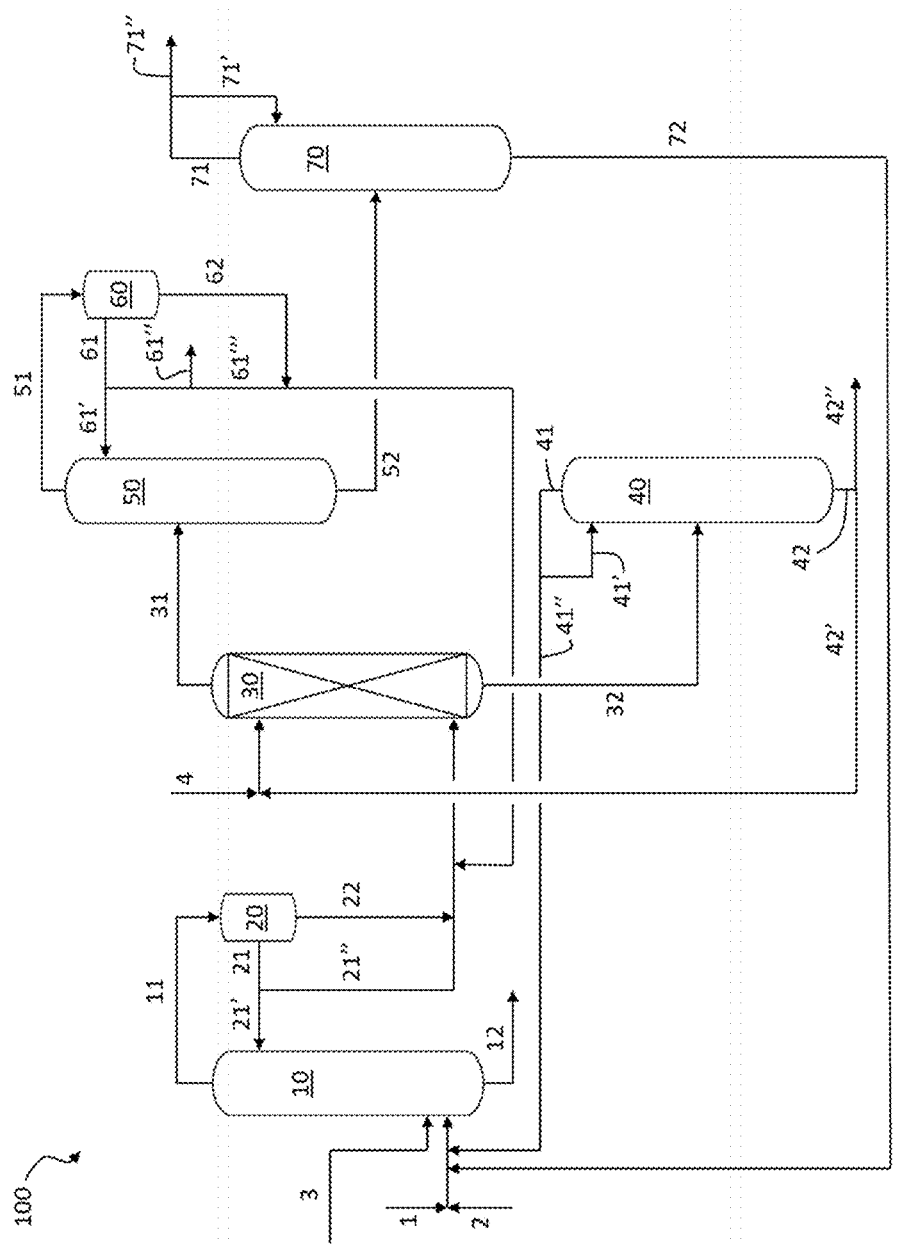

ACID CATALYZED SYNTHESIS OF METHYL ACRYLATE FROM ACRYLIC ACID AND METHANOL

FIELD OF THE INVENTION

The present invention relates to a process for the acid catalyzed synthesis of methyl acrylate from acrylic acid and methanol.

BACKGROUND OF THE INVENTION

Various processes for preparing (meth)acrylates from (meth)acrylic acid and alcohols using acid catalysts have been proposed.

U.S. Patent Application Publication No. 2004/0236143 discloses a process in which (meth)acrylates are prepared by reacting (meth)acrylic acid, which may be a crude (meth) acrylic acid, with an alcohol in the presence of at least one acid catalyst. In the process, acrylic acid is reacted in the presence of at least one acid catalyst with the alcohol in a reaction zone connected to a distillation unit. The (meth) acrylic acid, along with the low boilers, Michael adducts, and water of reaction are condensed and sent to a scrubbing unit to be treated with a wash liquid. The discharge from the wash step is separated into an organic phase and an aqueous phase, and some of the organic phase is passed as reflux in the distillation unit while the remainder is subjected to low boiler removal, where the organic phase from the distillate is subjected to a further distillation unit. The bottom product of the low boiler removal operation is subjected to purifying distillation to provide the desired ester.

The conventional processes for acid catalyzed synthesis of methyl acrylate are inefficient and require large quantities of wash liquid and energy.

There is a need for more efficient processes that address one or more of these issues.

SUMMARY OF THE INVENTION

The present invention is directed to methods for preparing methyl acrylate.

According to one aspect of the present invention, a method for preparing methyl acrylate comprises:
a) heating in a reaction zone a mixture comprising acrylic acid, methanol, and an acid catalyst to react and form a product comprising methyl acrylate which is vaporized with other light components and then fed to a distillation zone, wherein a feed stream entering the reaction zone comprises methanol to acrylic acid in a molar ratio of greater than 1 and less than 2, and a residence time in the reaction zone ranges from 0.25 to 2 hours;
b) condensing and phase-separating a distillate from the distillation zone to form an organic phase comprising methyl acrylate and an aqueous phase;
c) returning a portion of the organic phase to the distillation zone as organic reflux; and
d) feeding the remainder of the organic phase and the aqueous phase of the distillation zone to an extraction column to form a methanol rich aqueous effluent and an organic effluent comprising methyl acrylate.

BRIEF DESCRIPTION OF THE DRAWINGS

The FIGURE shows a schematic representation according to one embodiment according to the present invention.

DETAILED DESCRIPTION OF EMBODIMENTS OF THE INVENTION

As used herein, the terms "a," "an," "the," "at least one," and "one or more" are used interchangeably. The terms "comprises," "includes," "contains," and variations thereof do not have a limiting meaning where these terms appear in the description and claims. Thus, for example, a mixture that includes a polymerization inhibitor can be interpreted to mean that the mixture comprises at least one polymerization inhibitor.

As used herein, recitations of numerical ranges by endpoints includes all numbers subsumed in that range (e.g. 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.1 to 100, from 1 to 99.99, from 1.01 to 99.99, from 40 to 6, from 1 to 55, etc.

As used herein, the recitations of numerical ranges and/or numerical values, including such recitations in the claims, can be read to include the term "about." In such instances, the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety or its equivalent U.S. version is so incorporated by reference) especially with respect to the disclosure of definitions (to the extent not inconsistent with any definitions specifically provided in this disclosure) and general knowledge in the art.

One aspect of the present invention relates to a method for preparing methyl acrylate comprising heating in a reaction zone, a mixture comprising acrylic acid, methanol, and an acid catalyst to react and form a product comprising methyl acrylate. The reaction within the reaction zone occurs in the liquid phase.

In the inventive process, the feed stream to the reaction zone comprises a molar excess of methanol with respect to acrylic acid, i.e., the molar ratio of methanol to acrylic acid fed to the reaction zone is greater than 1. The molar ratio of methanol to acrylic acid is the molar ratio of the methanol to acrylic acid in the combined feed stream fed to the reaction zone, which may include both fresh feed entering into the system and recycle streams from other unit operations within the system. As used herein, the terms "combined feed stream" and "feed stream" means all of the reactants entering the reaction zone, including reactants entering the system (i.e., fresh feed) and reactants recycled from other unit operations in the system.

For example, the molar ratio of methanol to acrylic acid fed to the reaction zone may be greater than or equal to 1.05, 1.1, 1.2, 1.3, 1.4, 1.5, 1.6, 1.7, or 1.8. Preferably, the molar ratio of methanol to acrylic acid is greater than or equal to 1.1. More preferably, the molar ratio of methanol to acrylic acid is greater than or equal to 1.2. Even more preferably, the molar ratio of methanol to acrylic acid is greater than or equal to 1.3.

The molar ratio of methanol to acrylic acid may be less than or equal to 2. For example, the molar ratio of methanol to acrylic acid may be less than or equal to 1.9, 1.8, 1.7, 1.6, or 1.5. Preferably, the molar ratio of methanol to acrylic acid is less than or equal to 1.8. More preferably, the molar ratio of methanol to acrylic acid is less than or equal to 1.7. Even more preferably, the molar ratio of methanol to acrylic acid is less than or equal to 1.6.

The molar ratio may be a range between any of endpoints disclosed above. For example, the molar ratio may range from 1.1 to 1.8, from 1.2 to 1.9, from 1.3 to 1.6, etc. Preferably, the molar ratio of the methanol to acrylic acid fed to the reaction zone ranges from 1.1 to 1.8. More preferably, the molar ratio of methanol to acrylic acid ranges from 1.2 to 1.7. Even more preferably, the molar ratio of methanol to acrylic acid ranges from 1.3 to 1.6.

The acrylic acid introduced into the process is preferably an overhead grade of acrylic acid, which has been distilled to remove heavy ends components such as dimer (e.g., Michael adducts) and maleic acid. The acrylic acid fed to the system may comprise at least 98 wt. % acrylic acid, such as, for example, at least 98.5 wt. % acrylic acid or at least 99 wt. % acrylic acid. Preferably, the acrylic acid is substantially free of impurities, such as Michael adducts and acetic acid. As used herein, the term "substantially free of impurities" means that the acrylic acid contains less than 2 wt. % of impurities, preferably less than 1.5 wt. % of impurities, and more preferably, less than 1 wt. % of impurities.

The mixture introduced into the system (i.e., the fresh feed stream) may comprise, consist essentially of, or consist of acrylic acid, methanol, acid catalyst, and, optionally, a polymerization inhibitor. As used herein, "consist essentially of acrylic acid, methanol, and acid catalyst" means that the fresh feed stream does not include any impurities that will foul the system or adversely affect the yield of methyl acrylate. As used herein, the term "fresh feed stream" means the material entering into the system and excludes any materials that are recycled within the system. Preferably, the fresh feed stream is fed continuously to the system such that the process is a continuous process.

If a lower grade acrylic acid is used, the acrylic acid may be purified by any known process prior to being fed to the reaction zone.

Polymerization inhibitors may include alkylphenols, e.g. o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol or 2,2'-methylenebis(6-tert-butyl-4-methyphenol); hydroxyphenols, e.g. hydroquinone, 2-methylhydroquinone, 2,5-di-tert-butylhydroquinone, pyrocatechol (1,2-dihydroxybenzene) or benzoquinone; aminophenols, e.g. para-aminophenol; nitrosophenols, e.g. para-nitrosophenol; alkoxyphenols, e.g. 2-methoxyphenol (guajacol, pyrocatechol monomethyl ether), 2-ethoxyphenol, 2-isopropxyphenol, 4-methoxyphenol (hydroquinone monomethyl ether), mono- or di-tert-butyl-4-methoxyphenol; tocopherols, e.g. α-tocopherol, and 2,3-dihydro-2,2-dimethyl-7-hydroxybenzofuran (2,2-dimethyl-7-hydroxy-coumarane); N-oxyls, e.g. 4-hydroxy-2,2,6,6-tetramethylpiperidin-N-oxyl, 4-oxo-2,2,6,6-tetramethylpiperidin-N-oxyl, 4-acetoxy-2,2,6,-6-tetramethylpiperidin-N-oxyl, 2,2,6,6-tetramethylpiperidin-N-oxyl, 4,4',4"-tris(2,2,6,6-tetramethylpiperidin-N-oxyl) phosphite or 3-oxo-2,2,5,5-tetramethylpyrrolidin-N-oxyl; aromatic amines or phenylenediamines, e.g. N,N-diphenylamine, N-nitrosodiphenylamine, N,N'-dialkyl-para-phenylenediamine; hydroxylamines, e.g. N,N-diethylhydroxylamine; phosphorus-containing compounds, e.g. triphenylphosphine, triphenyl phosphite, hypophosphorous acid or triethyl phosphite; sulfur-containing compounds, e.g. diphenyl sulfide or phenothiazine. When included in the feed stream, the polymerization inhibitor may be present in an amount ranging from 0.01 to 0.1 wt. %. Additional polymerization inhibitor may be added elsewhere in the system as desired.

The acid catalyst may comprise sulfuric acid or a sulfonic acid, such as, for example, p-toluenesulfonic acid (PTSA), benzenesulfonic acid, dodecylbenzenesulfonic acid, methanesulfonic acid (MSA), and mixtures thereof. Preferably, the acid catalyst is sulfuric acid.

The acid catalyst may be present in an amount ranging from 1 to 10 wt. % based on the total weight of the liquid bleed, i.e., the bottoms stream exiting the reaction zone. Preferably, the acid catalyst is present in an amount ranging from 2 to 8 wt. % relative to the total weight of the bottoms stream exiting the reaction zone. More preferably, the acid catalyst is present in an amount ranging from 3 to 7 wt. % relative to the total weight of the bottoms stream exiting the reaction zone.

The reaction zone has a volume that provides the feed stream with a residence time of at least 0.25 hours. For example, the volume of the reaction zone provides the feed stream with a residence time of at least 0.35 hours or at least 0.5 hours. Preferably, the residence time of the reaction zone is at most 2.5 hours, such as, at most 2 hours, at most 1.5 hours, or at most 1 hour.

The products may exit the reaction zone as either a vapor, which enters the distillation zone, or as the liquid bleed. The liquid bleed can be disposed of as organic waste. The liquid bleed may comprise less than 5 wt. % based on the total amount of reactants entering the system, i.e., the combined feed stream.

The temperature within the reaction zone may range from 60 to 160° C., preferably from 70 to 150° C., more preferably from 90 to 140° C., and even more preferably from 100 to 130° C. The column may be operated at atmospheric pressure. Therefore, the reaction zone may be operated at slightly above atmospheric pressure, such as, for example, 0.1 to 5 psig.

As used herein, the term "reaction zone" refers to where the reaction of the acrylic acid with methanol takes place in the presence of an acid catalyst. The reaction zone may comprise, for example, a reactor, such as a glass-lined vessel, having a reboiler to provide heating to reaction temperature and boil-up for product/lights removal or separation from the catalyst, or the bottom stage of a distillation column. Preferably, the reaction zone comprises a reactor that acts as a sump to a distillation column.

As used herein, the term "distillation zone" refers to an area in a distillation column in which the separation of components takes place. The distillation zone may comprise a distillation column connected to a reactor (i.e., the reaction zone). When the reaction zone comprises the bottom stage of a distillation column, the distillation zone may comprise the other stages of the distillation column. Preferably, the distillation zone comprises a distillation column, which is connected to a separate reactor comprising the reaction zone, and functions as the column's bottom stage.

The distillate from distillation zone may be condensed by any conventional means, such as, for example a shell and tube condenser, to form a condensate comprising a 2-phase distillate product. The condensate may be phase-separated to form an organic phase and an aqueous phase. The phase-separation may be performed in any liquid-liquid separator known in the art, such as, for example, a decanter. The organic phase comprises primarily organic components including methyl acrylate. The aqueous phase comprises water formed in the reaction zone, as well as soluble fractions of organic materials, which include methanol and methyl acrylate.

A portion of the organic phase may be returned to the distillation zone as organic reflux. The portion of the organic phase returned to the distillation zone may comprise up to 67 wt. % of the total amount of the organic phase from the phase separator. Preferably, the portion of the organic phase returned to the distillation zone as reflux comprises at least 5 wt. % of the total amount of the organic phase from the phase separator, such as, at least 10 wt. %, at least 15 wt. %, at least 20 wt. %, at least 25 wt. %, at least 30 wt. %, or at least 40 wt. % of the total amount of the organic phase from the phase separator. Preferably, the portion of the organic phase returned to the distillation zone comprises less than 67 wt. %, less than 60 wt. %, less than 55 wt. %, or less than 50 wt. % of the total amount of the organic phase from the phase separator. Increasing the amount of the portion of organic phase returned to the distillation zone as reflux may increase the purity of the methyl acrylate product leaving the distillation zone but may also increase the equipment size and energy required.

The remainder of the organic phase, i.e., the organic phase not returned to the distillation zone as reflux, may be fed to an extraction column. The aqueous phase may be combined with the remainder of the organic phase and fed to the extraction column.

In the extraction column water is used to perform bulk separation of the excess methanol from the organic phase. The extraction column provides a methanol rich aqueous effluent and an organic effluent comprising primarily methyl acrylate. The methanol rich aqueous effluent also comprises soluble methyl acrylate.

The methanol rich aqueous effluent may then be fed to an alcohol recovery column. The alcohol recovery column may comprise a distillation column in which the methanol rich aqueous effluent is distilled to separate the water from the methanol and other organic components more volatile than water. The bottoms stream comprises water and is substantially free of organics more volatile than water.

As used herein, the term "substantially free of organics more volatile than water" refers to a bottoms stream that comprises less than 2 wt. % of organics more volatile than water based on the total weight of the bottoms stream, preferably less than 1 wt. % of organics more volatile than water, and more preferably less than 0.5 wt. % of organics more volatile than water. Preferably the bottoms stream is substantially comprised of water. As used herein, the term "substantially comprised of water" means that the bottoms stream comprises at least 97 wt. % water based on the total amount of the bottoms stream, preferably at least 98 wt. % water, more preferably at least 99 wt. % water, and even more preferably at least 99.5 wt. % water.

The distillate from the alcohol recovery column comprises methanol and organic components more volatile than water, including methyl acrylate. The distillate from the alcohol recovery column may be totally or partially condensed, and a portion of the condensed distillate may be returned to the alcohol recovery column as reflux. This reflux may comprise, for example, at least 65 wt. % of the total weight of the condensed distillate. Preferably, the portion of the condensed distillate fed to the alcohol recovery column as reflux may comprise at least 75 wt. % of the total weight of the condensed distillate, more preferably, at least 85 wt. %. The remainder of the distillate from the alcohol recovery column may be recycled to the reaction zone.

The bottoms stream from the alcohol recovery column may be disposed of as waste. Alternatively, a portion of the bottoms stream from the alcohol recovery column may be recycled and fed to the extraction column with the water used for the bulk separation of the excess alcohol from the organic phase. Preferably, a portion of the bottoms stream is recycled.

The organic effluent from the extraction column may be fed to a lights removal column to separate the organic effluent into a distillate comprising organics more volatile than methyl acrylate and a bottoms stream.

The distillate from the lights removal column may comprise methanol, water, and methyl acetate. The distillate from the lights removal column may be partially condensed and the liquid distillate separated into an organic phase and an aqueous phase. Some light impurities are not condensed and may be allowed to leave the process as vapors via a condenser vent system. A portion of the organic phase may be returned to the lights removal column as organic reflux. For example, the portion of the organic phase returned to the lights removal column as reflux comprises at least 50 wt. % of the total amount of the organic phase from the phase separator, such as, at least 60 wt. %, at least 70 wt. %, at least 80 wt. %, or at least 90 wt. % of the total amount of the organic phase from the phase separator. The remainder of the organic phase may be recycled to the feed of the extraction column. The aqueous phase may also be recycled back to the extraction column to be combined with the feed to the extraction column along with the remainder of the organic phase.

Preferably, less than 15 wt. % of the total amount of the feed entering the lights removal column is removed as light ends in the distillate. More preferably, less than 13 wt. % of the total amount of the feed entering the lights removal column is removed as light ends in the distillate. Even more preferably, less than 11 wt. % of the total amount of the feed entering the lights removal column is removed as light ends in the distillate.

Occasionally, a small fraction of the organic phase from the lights removal column is bled from the system to facilitate light ends removal that has built up in the process.

The bottoms stream from the lights removal column may be fed to a refining column.

In the refining column, the bottoms stream from the lights removal column is separated to form a distillate comprising methyl acrylate and a bottoms stream comprising heavy components less volatile than methyl acrylate. Preferably, the distillate from the refining column comprises at least 85 wt. % of the total amount of the feed to the refining column. More preferably, the distillate from the refining column comprises at least 90 wt. % of the total amount of the feed to the refining column, and even more preferably comprises at least 95 wt. % of the total amount of the feed to the refining column.

The distillate from the refining column may be condensed and a portion of the condensed distillate may be fed to the refining column as reflux. The remainder of the condensed distillate forms a methyl acrylate product stream. The portion of the condensed distillate fed to the refining column as reflux may comprise, for example, at least 10 wt. % of the total weight of the condensed distillate. Preferably, the portion of the condensed distillate fed to the refining column as reflux may comprise at least 20 wt. % of the total weight of the condensed distillate, more preferably, at least 45 wt. %.

The product stream may comprise at least 98 wt. % methyl acrylate relative to the total weight of the product stream. Preferably, the product stream comprises at least 99 wt. % methyl acrylate, and more preferably, at least 99.5 wt. % methyl acrylate.

The bottoms stream from the refining column may be recycled to the reaction zone to recover additional methyl acrylate that may have exited the refining column in the bottoms stream.

One embodiment of a process according the present invention is shown schematically in the FIGURE. The system 100 has a reactor column 10 which is fed by a fresh feed of acrylic acid 1, methanol 2, and an acid catalyst 3. The fresh feed enters the bottom stage of reactor column 10, which is heated and acts as the reaction zone. A liquid bleed 12 exits the bottom stage of the reactor column 10. The upper stages of the reactor column 10 act as a distillation zone to rectify the reaction products, and the distillate 11 exits the top of the reactor column 10.

The distillate 11 from the reactor column 10 is condensed and then separated into an organic phase 21 and an aqueous phase 22 in decanter 20. A portion 21' of the organic phase 21 is returned to reactor column 10 as reflux, and the remainder 21" of the organic phase 21 is combined with the aqueous phase 22 and fed to an extraction column 30.

Fresh water feed 4 enters the top of the extraction column 30 and is used for bulk separation of excess methanol. A methanol rich aqueous effluent 32 exits the bottom of the extraction column 30, and an organic effluent 31 exits the top of the extraction column 30.

The methanol rich aqueous effluent 32 is fed to an alcohol recovery column 40, where a distillate 41 exits the top of the alcohol recovery column 40 and a bottoms stream 42 exits the bottom of the alcohol recovery column 40. A portion 41' of the distillate 41 is returned to the column as reflux and the remainder 41" of the distillate 41 is recycled back to the reactor column 10 to join the feed stream. A portion 42' of the bottoms stream 42 of the alcohol recovery column 40 is recycled to the top of extraction column 30 to join fresh water feed 4, and the remainder 42" of bottoms stream 42 is sent to waste.

The organic effluent 31 from extraction column 30 is fed to lights removal column 50. The distillate 51 of lights removal column 50 is condensed and then separated into an organic phase 61 and an aqueous phase 62 in decanter 60. A portion 61' of organic phase 61 exiting decanter 60 is returned to the lights removal column 50 as reflux, another portion 61" of organic phase 61 is bled from the system, and the remainder 61'" of the organic phase 61 is combined with the aqueous phase 62 to be recycled back to the extractor column 30 to enter with the reactor column distillate 21" and 22 feed to the extractor.

The bottoms stream 52 of the lights removal column 50 is fed to a refining column 70. A distillate 71 exits the top of the refining column 70 and a portion 71' of the distillate 71 is returned to the column as reflux and the remainder 71" of the distillate 71 comprises the methyl acrylate product. The bottoms stream 72 is recycled to the reactor column 10.

In the FIGURE, the combined feed to the reactor column 10 is comprised of the fresh feed (i.e., acrylic acid 1, methanol 2, and acid catalyst 3), as well as the distillate 41 from the alcohol recovery column 40 and the bottoms stream 72 from the refining column 70.

Example

The following example illustrates the present invention but is not intended to limit the scope of the invention.

In the present example, a feed mixture was fed at a rate of 938 g/h to the bottom stage of a glass Oldershaw 2" diameter reactor column with a working sump volume of 550 ml and 14 trays for rectification. The feed mixture was made with a grade of acrylic acid that had been distilled to remove heavy end components, including dimer (e.g., Michael adducts) and maleic acid, and which contained 0.05 wt. % of phenothiazine for inhibition. The feed mixture bulk composition was 50.9 wt. % acrylic acid, 34 wt. % methanol, 14.4 wt. % methyl acrylate and 0.7 wt. % water, which resulted in a molar ratio of methanol to acrylic acid of 1.5. Small quantities of 98 wt. % sulfuric acid were also added to the column bottom stage as needed to maintain the composition in the bottom stage at 5 wt. % sulfuric acid as measured by acid titration. Also, approximately 14 g/h of inhibitor solution was added to the condenser, which was composed of 1.2 wt. % phenothiazine and 1.2 wt. % hydroquinone in methyl acrylate. Additionally, 5 g/h of inhibitor solution was added to the reflux return line to the column, which was composed of 1.2 wt. % phenothiazine in methyl acrylate.

The reactor column bottoms stage was heated to maintain a temperature of 120° C., and the vapor product was fed to the distillation column operating at atmospheric pressure above the top tray, while the column bottom stage was operated at slightly above atmospheric pressure (0.2 psig) as determined by the pressure drop through the Oldershaw column. An 8 g/h liquid bleed composed of 23 wt. % acrylic acid, 55 wt. % dimer of acrylic acid, 6 wt. % methyl acrylate, 2 wt. % methanol, 5 wt. % sulfuric acid, 6 wt. % water and balance heavy byproducts comprising less than 1 wt. % of the total amount fed to the reactor, was drawn from the bottom stage for level control.

The reaction products were rectified as they passed through the distillation column and the overhead vapors were condensed to produce a two-phase distillate product, which was separated into an organic phase and an aqueous phase. The organic phase was mostly methyl acrylate with 10.4 wt. % water, 9.4 wt. % methanol, 0.6 wt. % acrylic acid, 0.4 wt. % methyl acetate and smaller quantities of other trace impurities. The aqueous phase was water with 24.1 wt. % methanol, 13.8 wt. % methyl acrylate, 0.3 wt. % acrylic acid and smaller quantities of other trace impurities. About 33 wt. % of the condensed organic phase was returned to the distillation column as reflux, and the remainder of the organic phase and the aqueous phase were sent to an extraction column.

The extraction step was performed at atmospheric conditions using a KARR® Column Bench Top Unit, model BTU-48, with a ⅝" internal diameter by 48" long active region. Water containing 0.005 wt. % hydroquinone was fed at a rate of 390 g/h to the top of the column to perform the bulk separation of the excess methanol from the organic phase, which was fed to the bottom of the extractor column. A stream containing 95 wt. % methyl acrylate, 5 wt. % methyl acetate was also fed to the bottom of the extractor column at a flow rate of 60 g/h to simulate the distillate recycle from the lights removal column. A methanol rich aqueous effluent composed of water with 14 wt. % methanol, 7 wt. % methyl acrylate, 0.2 wt. % acrylic acid and smaller quantities of other trace impurities was collected at a rate of 630 g/h from the bottom of the column to be fed to an alcohol recovery column to recover the methyl acrylate and excess methanol. The organic effluent from the extractor was methyl acrylate with 3.2 wt. % water, 1 wt. % methyl acetate, 0.5 wt. % acrylic acid, 0.4 wt. % methanol, and smaller quantities of trace impurities, was collected at a rate of 730 g/h from the top of the extractor column to be fed to the light ends removal column.

An extractor aqueous effluent was fed to an alcohol recovery column, a 2" Oldershaw column with 31 trays, a feed on tray 22 and run at atmospheric conditions, for recovery of methanol and methyl acrylate. The extractor aqueous effluent was composed of water with 9.5 wt. % methanol, 5.5 wt. % methyl acrylate, 0.1 wt. % acrylic acid, and smaller quantities of trace impurities, and was fed to the alcohol recovery column at an average rate of 950 g/h. The condenser was fed 11 g/h of inhibitor solution containing 5 wt. % hydroquinone in methyl acrylate. The alcohol recovery column was operated with a distillate to feed ratio of 0.19 and about 89% of the distillate was returned to the column as reflux. The distillate average bulk composition was 54 wt. % methanol, 44 wt. % methyl acrylate, 1.3 wt. % water and trace heavies, and would be recycled back to the reactor as feed. The bottoms of the alcohol recovery column was composed of water with 0.1 wt. % methyl acrylate, 0.1 wt. % acrylic acid and smaller quantities of other trace components.

An extractor organic effluent was fed to a lights removal column, a 2" Oldershaw column with 31 trays, a feed on tray 14 and run at a top pressure of 600 mmHg absolute, to remove light ends, which included methanol and methyl acetate. The extractor organic effluent consisted of methyl acrylate with 3.2 wt. % water, 2.3 wt. % methyl acetate, 0.5 wt. % acrylic acid, 0.4 wt. % methanol and 1 wt. % of other impurities, and was fed to the light ends removal column at an average rate of 660 g/h. Also, approximately 15 g/h of inhibitor solution was added to the condenser, which was composed of 1.2 wt. % phenothiazine and 1.2 wt. % hydroquinone in methyl acrylate. Additionally, 5 g/h of inhibitor solution was added to the reflux line to the column, which was composed of 1.2 wt. % phenothiazine in methyl acrylate. The lights removal column was operated so that the distillate was condensed to produce a two-phase distillate product, which was separated into an organic phase and an aqueous phase, and a portion of the organic phase was recycled back to the column. The lights removal column was operated so that about 92% of the organic distillate was returned to the column as reflux, and the remainder of the organic distillate, 41 g/h, combined with the aqueous distillate, 20 g/h, was about 10 wt. % of the light removal column feed stream and could be recycled back to the extractor feed.

The bottoms of the lights removal column were fed to a refining column, a 1.25" Oldershaw column with 16 trays, a feed to tray 6 and operated at 300 mmHg absolute top pressure. The column was also feed approximately 8 g/h of inhibitor solution added to the condenser and 15 g/h of inhibitor solution added to the reflux line to the column, where both inhibitor solutions were composed of 0.1 wt. % hydroquinone monomethyl ether in methyl acrylate. The refining column was operated so that 44% of the distillate was returned to the column as reflux, and the distillate product to feed ratio was 90%. The 555 g/h distillate product composition was 99.78 wt. % methyl acrylate with 0.1 wt. % methanol, 0.1 wt. % methyl propionate and 0.02 wt. % water. The 54 g/h bottoms stream composition was 84 wt. % methyl acrylate, 6 wt. % acrylic acid and 10 wt. % other heavies.

The bottoms from the refining column were recycled to the reactor to recover methyl acrylate and to permit any heavy components to leave in the liquid reactor bleed.

We claim:

1. A method for preparing methyl acrylate, comprising:
   a) heating in a reaction zone a mixture comprising acrylic acid, methanol, and an acid catalyst to react and form a product comprising methyl acrylate, which is vaporized with other light components and then fed to a distillation zone, wherein a feed stream entering the reaction zone comprises methanol to acrylic acid in a molar ratio of greater than 1 and less than 2, and a residence time in the reaction zone ranges from 0.25 to 2 hours;
   b) condensing and phase-separating a distillate from the distillation zone to form an organic phase comprising methyl acrylate and an aqueous phase;
   c) returning a portion of the organic phase to the distillation zone as organic reflux; and
   d) feeding the remainder of the organic phase and the aqueous phase of the distillation zone to an extraction column to form a methanol rich aqueous effluent and an organic effluent comprising methyl acrylate.

2. The method according to claim 1, wherein the acid catalyst is sulfuric acid or a sulfonic acid.

3. The method according to claim 1, wherein acrylic acid entering the reaction zone as fresh feed comprises less than 2 wt. % impurities.

4. The method according to claim 1, further comprising feeding the methanol rich aqueous effluent from the extraction column to an alcohol recovery column to form a distillate comprising methanol and a bottoms stream substantially free of organics more volatile than water.

5. The method according to claim 4, wherein at least a portion of the distillate of the alcohol recovery column is recycled to the reaction zone.

6. The method according to claim 4, wherein a portion of the bottoms stream of the alcohol recovery column is recycled to the extraction column.

7. The method according to claim 1, further comprising feeding the organic effluent from the extraction column to a lights removal column to separate the organic effluent into a distillate comprising organics more volatile than methyl acrylate and a bottoms stream.

8. The method according to claim 7, wherein the distillate comprising organics more volatile than methyl acrylate is at least partially condensed and phase separated into an organic phase and an aqueous phase, wherein at least a portion of the organic phase is returned to the light ends column as organic reflux and at least a portion of the remainder of the organic phase and the aqueous phase are recycled to the extraction column.

9. The method according to claim 7, wherein the bottoms stream of the light ends column is fed to a refining column to form a product stream comprising methyl acrylate and a bottoms stream comprising heavy components less volatile than methyl acrylate, wherein at least a portion of the bottoms stream of the refining column is recycled to the reaction zone.

10. The method according to claim 1, wherein the reaction zone is operated at a temperature ranging from 60 to 150° C. and the acid catalyst comprises sulfuric acid in an amount ranging from 2 to 8 wt. % relative to the total weight of a bottoms stream exiting the reaction zone.

* * * * *